United States Patent [19]

Dell

[11] Patent Number: 4,542,012

[45] Date of Patent: Sep. 17, 1985

[54] FILM-FORMING COMPOSITION CONTAINING AN ANTIMICROBIAL AGENT AND METHODS

[75] Inventor: John D. Dell, St. Paul, Minn.

[73] Assignee: Minnesota Mining and Manufacturing Company, St. Paul, Minn.

[21] Appl. No.: 465,806

[22] Filed: Feb. 11, 1983

Related U.S. Application Data

[63] Continuation-in-part of Ser. No. 394,882, Jul. 2, 1982, abandoned.

[51] Int. Cl.$^4$ ............ A61K 9/70; A61K 31/79; A61L 15/00
[52] U.S. Cl. ............................ 424/28; 424/78; 424/80; 128/156
[58] Field of Search ............ 424/28, 78, 80; 525/127, 128; 128/156; 528/75

[56] References Cited

U.S. PATENT DOCUMENTS 4,145,514 3/1979 De Vry et al. ............ 528/75
4,374,969 2/1983 Frisch, Jr. ............ 528/75

FOREIGN PATENT DOCUMENTS 2827450 1/1979 Fed. Rep. of Germany ........ 424/78

Primary Examiner—Sidney Marantz
Assistant Examiner—Shawn P. Foley
Attorney, Agent, or Firm—Donald M. Sell; James A. Smith; Robert W. Sprague

[57] ABSTRACT

A dermatologically acceptable, film-forming composition which comprises a film-forming polymer and, as a broad spectrum antimicrobial agent, iodine which forms a complex with the film-forming polymer. The compositions when applied to skin from a fugitive solvent form a substantially water-insoluble, tack-free, flexible film which adheres to skin, releases the antimicrobial agent when the film is in contact with skin, and exhibits an elongation of at least about 150%. A method of using the composition is also described.

20 Claims, No Drawings

FILM-FORMING COMPOSITION CONTAINING AN ANTIMICROBIAL AGENT AND METHODS

This application is a continuation-in-part of copending application U.S. Ser. No. 394,882, filed July 2, 1982, now abandoned.

This invention relates to a dermatologically acceptable, film-forming composition containing an antimicrobial agent. More specifically, it relates to film-forming compositions useful in promoting asepsis on skin. Methods of using the composition are also within the scope of the invention.

In order to control infection and promote healing in patients having surgical incisions or other open wounds, it has become standard hospital practice to apply an antimicrobial agent to the wound. The application of antimicrobial agents is also practiced during surgical operations to sterilize skin adjacent the incision site. Surgical incise drapes are also often employed in surgical operations to further promote asepsis in the operating field.

Topical application of antimicrobial agents has been accomplished using, for example, preoperative skin preps, surgical scrub tissues, washes, wound cleaners, lotions, and ointments. Since microorganisms may survive the initial application of the antimicrobial agent, it is often necessary to reapply the agent in order to provide continued asepsis. Also, since antimicrobial agents are often water-soluble and are therefore subject to removal from the wound site when the site is sponged, irrigated or the like, reapplication of the antimicrobial agent may be necessary to assure continued asepsis.

Topical application of antimicrobial agents has also been accomplished using surgical incise drapes which comprise an antimicrobial agent-containing pressure-sensitive layer. For example, U.S. Pat. Nos. 4,310,509 (Berglund et al.) and 4,323,557 (Rosso et al.) describe surgical incise drapes which comprise such an adhesive and provide continued asepsis. More specifically, the Berglund patent describes a pressure-sensitive adhesive composition which contains chlorhexidene or a complex of polyvinylpyrrolidone and iodine, chlorhexidine and iodine being particularly effective antimicrobial agents. The Rosso patent describes a pressure-sensitive adhesive comprising n-vinylpyrrolidone residues in the polymer backbone. Iodine is complexed with these residues.

Further, topical application of antimicrobial agents has been accomplished using film-forming compositions which are applied to skin as liquids and contain antimicrobial agents, e.g., see U.S. Pat. Nos. 2,804,073 (Gallienne et al.), 3,577,516 (Gould et al.), 3,608,070 (Nouvel) and 3,975,350 (Hudgin et al.). Film-forming compositions comprising iodine in the form of a complex with an n-vinylpyrrolidone-residue-containing polymer are also known to the art, e.g., see U.S. Pat. No. 3,216,983 (Shelanski et al.). The Shelanski patent describes what are described as relatively water-insoluble films obtained by reacting polyvinylpyrrolidone or polyvinylpyrrolidone/vinyl acetate copolymer with a diisocyanate. Iodine is complexed with the polyvinylpyrrolidone units contained in the resulting polymer. U.S. Pat. Nos. 4,156,066 (Gould), 4,156,067 (Gould) and 4,255,550 (Gould) describe polyurethane polymers containing lactone and hydroxyl groups in the backbone. The Gould patents mention that these polymers are useful in burn dressings which may additionally comprise a polyvinylpyrrolidone-iodine complex.

The prior art has not provided a film-forming composition which is totally acceptable from the standpoint of convenience, comfort, safety and efficacy in promoting asepsis on skin. A good film-forming composition should be dermatologically-acceptable and capable of application to skin conveniently as a solution in a dermatologically-acceptable, volatile solvent. The film resulting from application of such a solution should be bacteria-impermeable, water-insoluble, nontacky and should permit facile transmission of water vapor therethrough. It should adhere suitably to skin and be capable of releasing the antimicrobial agent onto the skin over a period of time to promote asepsis for a suitably long period of time. Additionally, the resulting film should exhibit a degree of elongation which assures it will retain its integrity during wound retraction. The film should be soluble in a dermatologically acceptable solvent such as a lower alkyl alcohol which may be used as or in a remover solution which is employed to remove the film once the surgical procedure has been completed.

The film-forming composition of the present invention successfully meets the aforementioned criteria. Certain film-forming compositions additionally provide a film that exhibits a balance of toughness and flexibility which permits it to be removed intact or substantially intact once the surgical procedure is completed, thereby obviating the need for a remover solution if employment of such is not desired.

BRIEF SUMMARY OF THE INVENTION

The present invention provides a dermatologically acceptable, film-forming composition comprising:
(a) a film-forming polymer which is the reaction product of (i) a prepolymer having a plurality of isocyanate functionalities, said prepolymer being the reaction product of a polyisocyanate and an isocyanate-reactive compound having a plurality of functional groups reactive with said polyisocyanate; (ii) a polyvinylpyrrolidone polymer which is the free-radical-polymerization reaction product of at least n-vinylpyrrolidone and a vinyl-functional compound; and (iii) a chain-extender for the prepolymer and the polyvinylpyrrolidone polymer; the vinyl-functional compound being further characterized in that it contains a functionality having reactivity with the chain-extender which is substantially equivalent to the reactivity of the isocyanate functionalities of the prepolymer (i) with the chain-extender (iii); and
(b) as an antimicrobial agent, iodine which forms a complex with the film-forming polymer.

The composition, when applied to skin from a fugitive solvent, is capable of forming a substantially water-insoluble, tack-free, flexible film which adheres to skin, releases the antimicrobial agent when the film is in contact with skin. The film is soluble in dermatologically acceptable solvents such as a lower alkyl alcohol and can therefore be removed from skin therewith. The film further exhibits an elongation of at least about 150% (and less than about 1000%). More preferably, the film exhibits an elongation of at least about 200% (and less than about 1000%). Most preferably the film exhibits an elongation of at least about 250% (and less than 1000%).

The preferred compositions of the present invention which are capable of forming a film which can be removed intact or substantially intact without the use of a remover solution further exhibit a tensile strength of at least about 1500 psi. Preferred compositions which are capable of forming such a film exhibit a tensile strength of at least about 2000 psi and an elongation of at least about 200% (and less than about 1000%). Most preferred compositions which are capable of forming such a film exhibit a tensile strength of at least about 2500 psi and an elongation of at least about 250% (and less than about 1000%).

The method of using the compositions of the present invention to cover skin with a film exhibiting antimicrobial activity and to thereby promote asepsis comprises the steps of:

(a) applying the composition to the skin; and
(b) allowing the composition to dry to form a film.

The film may then be removed from skin conveniently by employment of a remover solution or the film may simply be allowed to wear off. Alternatively, a film exhibiting a tensile strength of at least about 1500 psi and an elongation of between about 150% and 1000% may also be removed substantially intact from skin by simply peeling the film therefrom.

The present invention solves the problems associated with prior art compositions by providing a film-forming composition which exhibits the following characteristics. The film-forming composition is dermatologically acceptable and may be applied to skin conveniently as a solution in a dermatologically acceptable, volatile solvent such as ethanol or isopropanol. Due to the nature of the film-forming polymer, the composition of the invention does not require the presence of a fugitive plasticizer. The film resulting from the application of the composition is bacteria-impermeable and substantially water-insoluble and nontacky. Also, the film adheres suitably to skin and releases the antimicrobial agent contained therein to skin upon contact of the film with skin. The film is soluble in dermatologically-acceptable lower alkyl alcohols such that it may be removed conveniently using a remover solution comprising such an alcohol. Also, certain compositions of the invention provide a film which exhibits a balance of toughness and flexibility properties which permits it to be removed intact or substantially intact from the patient once the surgical procedure has been completed without employment of a remover solution, if such a method of removal is preferred. Since the film-forming compositions of the invention are applied to skin from solutions, complete conformability of the resulting films to the contours of the patient is assured. This feature is particularly desirable when the compositions are used in surgical procedures in place of conventional incise drapes. The compositions of the invention are particularly suitable for use as pre-surgical skin preparations. The comopsitions are also suitable for promoting asepsis in and around puncture wounds such as sites of injection or catheterization.

DETAILED DESCRIPTION OF THE INVENTION

The compositions of the present invention are dermatologically-acceptable and dry to form a film which is substantially water-insoluble. As used in the instant specification and claims, the term "dermatologically acceptable" means that the composition does not cause substantial irritation when in contact therewith. As used in the instant specification and claims, the phrase "substantially water-insoluble" means that the film formed from the compositions of the present invention retains its integrity when contacted with bodily fluids, irrigation fluids and the like.

The tensile strength and elongation values stated in the instant specification and claims are determined in accordance with the ASTM test which is entitled "Standard Test Method For Tensile Properties of Plastics" and designated ASTM-D-638-80, incorporated hereby reference. Specifically, the testing procedure followed is that for "Non-rigid Classification Specimen Type IV" found in ASTM-D-638-80. The films tested are solvent-cast onto release paper (e.g., Polyslik® S-8004 from H. P. Smith Co.) and have a thickness of about 1 mil (0.0025 centimeter) when dry. The jaw separation rate to be employed in the testing procedure is 20 inches per minute.

Suitable prepolymers (i) are obtained by reacting a polyfunctional isocyanate with an isocyanate-reactive compound which contains a plurality of functionalities which are reactive with the polyfunctional isocyanate and are selected from the group consisting of a hydroxy group, a primary amine group, a secondary amine group, a thiol and a combination of at least two of the foregoing. Preferred in the practice of the invention are isocyanate-reactive compounds having a plurality of functionalities selected from the group consisting of a hydroxy group, a primary amine group, a secondary amine group and a combination of at least two of the foregoing.

Most preferred in the practice of the present invention are diols and diamines (having two primary amine groups) in which the hydroxy and primary amine groups, respectively, are located at terminal positions in the compound. While isocyanate-reaction compounds having functionality of greater than 2 may be employed, it is preferred that such be employed in combination with a major amount of a difunctional compound. This is particularly the case where the film-forming polymer is to be used to provide a film which can be removed substantially intact from skin since employment of only isocyanate-reactive compounds having a functionality of greater than 2 may result in excessive crosslinking of the film-forming polymer and in films which do not exhibit the requisite elongation.

Generally, the isocyanate-reactive compound should have a molecular weight of between about 750 and 2500. Employment of only isocyanate-reactive compounds having a molecular weight of less than about 750 may result in films which do not exhibit suitable flexibility. Employment of only isocyanate-reactive compounds having a molecular weight of greater than about 2500 result in films which exhibit undesirable tackiness. It is therefore preferred that if an isocyanate-reactive compound having a molecular weight of less than about 750 or greater than about 2500 is used that it be employed with a major amount (on a weight basis) of an isocyanate-reactive compound of molecular weight between about 750 and 2500.

When the film-forming polymer is to be used to provide a film which can be removed substantially intact, it is preferred that the isocyanate-reactive compound have a molecular weight of between about 800 and 2000. Employment of only isocyanate-reactive compounds having a molecular weight of less than about 800 may result in films which do not exhibit flexibility or elongation required to permit them to be removed intact or substantially intact from skin. Employment of only isocyanate-reactive compounds having a molecular weight of greater than about 2000 may result in films which do not exhibit tensile strength required to permit the film to be removed substantially intact. It is therefore preferred that if an isocyanate-reactive compound having a molecular weight of less than about 800 or greater than about 2000 is used that it be employed with a major amount (on a weight basis) of an isocyanate-reactive compound of molecular weight between about 800 and 2000.

Examples of suitable polyols having two terminal hydroxy groups are polyester diols, e.g., Multrathane R-14 ® (a polyester having a molecular weight of about 2000, commercially available from Mobay Chemical Corp.), Niax ® Polyol PCP 0210 and 0230 (polycaprolactones having molecular weights of about 800 and 1240, respectively, commercially available from Union Carbide Corp.); and polyether diols, e.g., Niax ® PPG-1025 and Niax ® PPG-2025 (polyether diols of molecular weights of about 1000 and 2000, respectively, commercially available from Union Carbide Corp). A preferred polyol is above-described Niax ® PPG 1025. An example of a suitable polyamine having two terminal primary amine groups is "Jeffamine D-2000" (a polyoxypropylene amine of about 2000 molecular weight, commercially available from Jefferson Chemical). Suitable polyamines having two terminal secondary amine groups are those which are obtained from the above-specifically-discussed polyamines which are converted to polyamines having secondary amine groups via conventional techniques. Examples of suitable polythiols are polyethylene glycol dimercaptoacetates (e.g., the polyethylene glycol dimercaptoacetate of molecular weight of about 750, commercially available from Evans Chemetics) and polyethyleneglycol dimercaptopropionates (e.g., the polyethyleneglycol dimercaptopropionate of molecular weight of about 775 (commercially available from Evans Chemetic). It is to be understood that either a single type of isocyanate-reactive compound or mixtures of different types of isocyanate-reactive compounds may be employed in preparing the prepolymer (i).

The preferred polyfunctional isocyanates for preparing the prepolymer (i) are diisocyanates. While isocyanates having functionality of greater than two may be employed, it is generally preferred that such be employed in combination with a major amount of a diisocyanate. Use of major amounts of an isocyanate which has a functionality of greater than two should particularly be avoided where it is desired to remove the film substantially intact from skin since such may result in excessive crosslinking of the film-forming polymer and in films which do not exhibit the requisite elongation. Specific examples of suitable diisocyanates are dicyclohexylmethane-4,4'-diisocyanate (e.g., that commercially available under the trade designation "Desmodur W" from Mobay Chemical), 4,4'-diphenylmethane diisocyanate (e.g., that commercially available under the trade designation "Mondur M" from Mobay Chemical), 2,4- and 2,6-toluene diisocyanate (e.g., the mixture of the two isomers which is commercially available under the trade designation "Mondur 80" from Mobay Chemical), 3-isocyanatomethyl-3,5,5-trimethylcyclohexyl-isocyanate (e.g., that commercially available under the trade designation "IPDI" from Thorsen Chemical), trimethylhexamethylene diisocyanate (e.g., that commercially available under the trade designation "TMDI" from Thorsen Chemical). Mixtures of different types of polyfunctional isocyanates may also be employed. A preferred diisocyanate is the above-described aliphatic diisocyanate dicyclohexylmethane-4,4'-diisocyanate.

The amount of the polyfunctional isocyanate employed in preparing the prepolymer (i) is preferably sufficient to assure complete conversion of all functionality in the isocyanate-reactive compound to isocyanate functionality.

The reaction of the isocyanate-reaction compound and the polyfunctional isocyanate to form the prepolymer (i) is conducted using conventional techniques. For example, the prepolymer (i) may be prepared by combining the isocyanate-reactive compound, the polyfunctional isocyanate and a catalyst such as dibutyl tin dilaurate and heating the resulting mixture at 100° C. for several hours in the presence of an inert, dry atmosphere such as dry nitrogen.

The polyvinylpyrrolidone polymer (ii) is the free-radical polymerization reaction product of at least n-vinylpyrrolidone and a vinyl-functional compound having a functionality having reactivity with the chain-extender which is substantially equivalent to the reactivity of the isocyanate functionalities of the prepolymer (i) with the chain-extender (iii). By "substantially equivalent reactivity" is meant that the reactivity of the functional groups of the polyvinylpyrrolidone polymer (ii) is such that the film-forming polymer prepared from the prepolymer (i), the polyvinylpyrrolidone polymer (ii), and the chain extender (iii) contains substantial numbers of segments provided by the prepolymer (i) and the polyvinylpyrrolidone polymer (ii).

The preferred polyvinylpyrrolidone polymer (ii) is the free-radical-polymerization product of at least n-vinylpyrrolidone and a vinyl-functional compound having a functionality selected from the group consisting of an isocyanate group and an azlactone group.

Examples of vinyl-functional compounds which contain an isocyanate group and are suitable for preparing the polyvinylpyrrolidone polymer (ii) are isocyanate-functional acrylates and methacrylates. The preferred vinyl-functional compound is isocyanatoethylmethacrylate (obtained from Dow Chemical Co.). Another suitable vinyl-functional compound is the reaction product of hydroxyethyl acrylate and the above-described 3-isocyanto-methyl-3,5,5-trimethylcyclohexyl-isocyanate.

Examples of vinyl-functional compounds which contain an azlactone group are described in U.S. Pat. No. 4,304,705 (Heilmann et al.), incorporated herein by reference. The preferred azlactone is 2-vinyl-4,4-dimethyl-2-oxazolin-5-one, the preparation of which is described in the aforementioned U.S. patent.

It is to be understood that two or more different types of vinyl-functional compounds containing a functionality reactive with the chain-extender (iii) may be employed in preparing the polyvinylpyrrolidone polymer (ii). For example, the polyvinylpyrrolidone polymer (ii) may contain both isocyanate functionality and azlactone functionality.

It is also to be understood that minor amounts of other free-radical-polymerizable monomers such as ethyl acrylate, isooctyl acrylate and the like may be employed in the preparation of the polyvinylpyrrolidone polymer (ii). Most preferred is a polyvinylpyrrolidone polymer (ii) prepared from only n-vinylpyrrolidone and one or more vinyl-functional compounds having functionality reactive with the chain-extender (iii).

It is preferred that polyvinylpyrrolidone polymer (ii) contain a total of no more than about 10 weight percent of residue of the vinyl-functional compound which contains the functionality reactive with the chain-extender (iii). For preparing the preferred polyvinylpyrrolidone polymer (ii) which is prepared from only n-vinylpyrrolidone and a vinyl-functional compound having a functionality reactive to the chain-extender (iii), it is desirable for the weight ratio of the amount of n-vinylpyrrolidone to the amount of the vinyl-functional compound having isocyanate or azlactone-functionality employed be from about 99:1 to 90:10. Greater amounts of the vinyl-functional compound may result in excessive crosslinking of the film-forming polymer and in films which do not exhibit suitable elongation. Polyvinylpyrrolidone polymers (ii) prepared from n-vinylpyrrolidone and isocyanatoethylmethacrylate in weight ratios of from about 99:1 to 97:3 have been found to be particularly suitable in the practice of the invention. Also, a polyvinylpyrrolidone polymer (ii) prepared from n-vinylpyrrolidone and 2-vinyl-4,4-dimethyl-2-oxazolin-5-one in a weight ratio of 97:3 has been found to be particularly suitable.

The free-radical-polmerization reaction employed in preparing the polyvinylpyrrolidone polymer (ii) is conducted using conventional techniques. A preferred free-radical-generating source is azobisisobutyronitrile. Tert-dodecylmercaptan may be desirably employed as a chain transfer agent. Generally the reaction is conducted in an inert organic solvent such as acetone in an inert atmosphere.

To prepare the film-forming polymer, the prepolymer (i) and the polyvinylpyrrolidone polymer (ii) are chain-extended using a chain-extender (iii) which contains a plurality of functional groups reactive with the prepolymer (i) and the polyvinylpyrrolidone polymer (ii). The resulting film-forming polymer is believed to comprise a random distribution of segments provided by each of the prepolymer (i) and the polyvinylpyrrolidone polymer (ii).

The chain-extender (iii) contains a plurality of functional groups selected from the group consisting of a hydroxy group, a primary amine group, a secondary amine group, a thiol, and a combination of at least two of the foregoing. The preferred chain-extender (iii) contains a plurality of functional groups selected from the group consisting of a hydroxy group, a primary amine group, a secondary amine group, and a combination of at least two of the foregoing.

The preferred chain-extenders are diols and diamines. Aliphatic amines are most preferred since the chain-extension reaction may be conducted conveniently in ethanol or isopropanol, which solvents may serve as the fugitive solvent from which the compositions of the invention may be applied to skin. While chain-extenders having more than two functional groups may be employed in the practice of the invention, it is preferred that such be employed in combination with a major amount of a difunctional chain-extender. This is particularly the case when it is desired to remove the film substantially intact from skin since employment of only chain-extenders having a functionality of greater than two may result in excessive crosslinking of the film-forming polymer and in films which do not exhibit the requisite elongation. Specific examples of suitable diols are 1,4-butanediol, ethyleneglycol and diethylene glycol. Specific examples of suitable diamines are 3-aminomethyl-3,5,5-trimethylcyclohexylamine (e.g., that commercially available under the designation isophorone diamine from Thorsen Chemical), "Jeffamine D-230" (a polyether diamine commercially available from Jefferson Chemical Co.), ethylene diamine, tetramethylene diamine, hexamethylene diamine, 4,4'-diaminodicyclohexyl methane, 1,4-diaminocyclohexane, 4,4'-diamino-3,3'-dimethyldicyclohexyl methane, piperazine, trimethyl hexamethyl diamine, hexamethyl diamine, 1,3-propane diamine, 1,2-propane diamine, and methylene dianiline. The preferred amine is above-described 3-aminomethyl-3,5,5-trimethylcyclohexylamine. Mixtures of different types of chain-extenders may be employed.

The manner by which the film-forming polymer is formed depends to some extent upon the nature of the chain-extender (iii) employed. Generally, when the chain-extender (iii) is an aliphatic polyamine it is convenient to conduct the chain-extension reaction at room temperature as follows. The isocyanate-functional prepolymer (i) and the polyvinylpyrrolidone polymer (ii) are combined. The polyvinylpyrrolidone polymer (ii) may be conveniently prepared in acetone and may be combined with the prepolymer (i) as a solution in acetone. A solution of the aliphatic amine chain-extender in isopropanol is then added to the above mixture of the prepolymer (i) and the polyvinylpyrrolidone polymer (ii), with stirring, to form the film-forming polymer. Generally, when the chain-extender (iii) is an aromatic polyamine or a polyol, it is convenient to conduct the chain-extension reaction as follows. The isocyanate-functional prepolymer (i) and the polyvinylpyrrolidone polymer (ii) are dissolved in acetone. In this instance, however, the aromatic polyamine or the polyol are added to the above solution either as a neat liquid or as a solution in an inert solvent such as acetone and the reaction mixture is heated.

The relative amounts of the isocyanate-functional prepolymer (i), the polyvinylpyrrolidone polymer (ii), and the chain-extender (iii) employed in the preparation of the film-forming polymer may be varied so long as the composition remains capable of forming a substantially water-insoluble, substantially tack-free, flexible film which adheres to skin. It is preferred in preparing the film-forming polymer that the weight ratio of the amount of the polyvinylpyrrolidone polymer (ii) employed to the amount of the isocyanate-functional prepolymer (i) employed be from about 2:98 to 20:80. If the weight ratio for the polyvinylpyrrolidone polymer (ii) to the isocyanate-functional prepolymer (i) exceeds 20:80, the resulting film-forming polymer may not be suitably insoluble in water. The weight ratio of the polyvinylpyrrolidone polymer (ii) to the isocyanate-functional prepolymer (i) is more preferably from about 5:95 to 15:85 and most preferably from 7:93 to 12:88. If the film-forming polymer is to be employed to form a film which can be removed intact or substantially intact, the relative amount of the isocyanate-functional prepolymer (i), the polyvinylpyrrolidone polymer (ii), and the chain-extender (iii) employed in the preparation of the film-forming polymer may be varied so long as the composition remains capable of forming a film which, in addition to exhibiting the above-mentioned properties, exhibits a tensile of at least about 1500 psi and an elongation of between about 150% and 1000% when tested in accordance with ASTM-D-638-80 using a jaw separation rate of 20 inches per minute.

The amount of the chain-extender (iii) employed depends on a variety of considerations including the reactivity and functionality of the polyfunctional isocyanate employed in preparing the isocyanate-functional prepolymer (i), the reactivity and functionality of the chain-extender (iii), and the hardness of the segment provided by the chain-extender residue in the film-forming polymer. Generally, the amount of the chain-extender (iii) employed will be about 0.4 to 1.0 equivalents per equivalent of the sum total of the reactive functionality in the isocyanate-functional prepolymer (i) and the polyvinylpyrrolidone polymer (ii). Employment of less than about 0.4 equivalent of the chain-extender (iii) per equivalent of the sum total of the reaction functionality is the isocyanate-functional prepolymer (i) and the polyvinylpyrrolidone polymer (ii) may result in formation of films which exhibit an undersirable level of tackiness. Employment of more than one equivalent of the chain-extender (iii) may undesirably result in formation of films which contain free chain-extender and therefore, depending on the nature of the chain-extender (iii), may not be dematologically acceptable. When the film is to be removed substantially intact and when the isocyanate employed in preparing the isocyanate-functional prepolymer (i) is aliphatic and the chain-extender (iii) is an aliphatic amine, it is preferred that the amine be employed in an amount of about 0.8 to 1.0 equivalents per equivalent of the sum total of the reactive functionality in the isocyanate-functional prepolymer (i) and the polyvinylpyrrolidone polymer (ii).

The broad-spectrum antimicrobial agent which is included in the compositions of the present invention is iodine. It is believed that iodine forms a complex with the n-vinylpyrrolidone residues in the film-forming polymer and that iodine release from the films obtained from the compositions of the present invention is a function of the level of such n-vinylpyrrolidone residues in the film-forming polymer.

As a general statement, film-forming compositions comprising about 1 to 6 weight percent iodine based on the weight of the film-forming polymer have been found to provide films exhibiting suitable antimicrobial activity. The preferred amount of iodine included in the film-forming composition depends, in part, upon the ultimate thickness of the film which is to be formed on skin. A relatively thin film which is formed from a film-forming composition of a given iodine content of course contain less iodine than a relatively thick film which is formed from that same film-forming composition. If the film is to be removed from skin using a remover solution, it may be relatively thin (e.g., less than about 0.5 mil), whereas a film which is to be peeled from skin should be relatively thick (e.g., about 1-3 mils). A preferred film-forming composition for forming a film which is to be removed using a remover solution comprises about 5.2 weight percent iodine based on the weight of the film-forming polymer. On the other hand, a preferred film-forming composition for forming a film which is to be peeled from skin comprises about 2 weight percent iodine based on the weight of the film-forming polymer. In any case, as a general statement, it is preferred that iodine be present in a film-forming composition in such an amount that it is released from the resulting film substantially continously and substantially uniformly over a sustained period of time (e.g., 30 minutes or greater).

It is preferred that the iodine be added to the film-forming polymer as a solution in a solvent such as ethanol. The solution desirably also contains inorganic iodide (e.g., sodium or potassium iodide). A suitable iodine-containing solution comprises a 0.5:1 to 4:1 molar ratio of iodide:iodine. The preferred molar ratio is 2:1 iodide:iodine.

The composition of the present invention is preferably applied to skin as a solution in a fugitive solvent which evaporates at a suitable rate when the composition is in contact with skin. Examples of suitable solvents which solubilize the film-forming polymer and exhibit suitable volatility are ethanol and isopropanol. Acetone may also be used if it is employed in combination with one of the foregoing to provide a solvent system which solubilizes the film-forming polymer. An isopropanol solution comprising the preferred composition described in Example 1 in the amount of about 25% solids by weight has been found to be particularly suitable to apply a film which can be removed substantially intact once the surgical procedure has been completed. An applicator for applying uniform coating of the composition to skin such that the resulting film may easily be removed substantially intact is described in abandoned application U.S. Ser. No. 394,884 filed July 2, 1982 and commonly assigned, incorporated herein by reference. It has been found that a film having a uniform thickness of about 1 mil (0.0025 centimeter) can be removed from the skin substantially intact by simply peeling the film therefrom.

An ethanol-isopropanol solution comprising the preferred composition described in Example 3 in the amount of about 11% solids by weight has been found to be particularly suitable to apply a film which is to be removed from skin using a dermatologically acceptable lower alkyl alcohol. Use of such an ethanol-isopropanol solution having a lower solids content results in a thin film which exhibits a shorter tack-free time than a thicker film which is to be removed intact without employment of a remover solution. The preferred remover solution comprises isopropanol.

The invention is further illustrated by the following non-limiting example. Generally, the values stated for tensile strength and elongation in Examples 1-4 represent the average of 8 to 10 independent tests.

TEST METHOD A—SURFACE TACK

One method for determining whether a composition provides a film which exhibits tack is the following. Each composition was coated onto Scotchpar ® brand polyester film (commercially available from 3M) using a #26 wirewound coating rod (commercially available from R. D. Specialties, Webster, N.Y.). Each coating was allowed to dry for 15 minutes under conditions of 73° F. and 15% Relative Humidity. A 2"×2" piece of Red Cross Cotton (long fiber virgin purified cotton USP) which is commercially available from Johnson and Johnson Company, was placed on each coating and was overlayed with a metal plate and weight which totalled 102 g. After 60 seconds, each metal plate, weight, and cotton batting were removed and each coating was examined with the naked eye for the presence of fibers of cotton adhered thereto. A coating which dries suitably to a tack-free state will have essentially no visible fibers adhered thereto.

TEST METHOD B—WATER INSOLUBILITY

One method for determining whether a composition provides a film which is suitably water-insoluble is the following. Each composition was again applied to Scotchpar ® brand polyester film in the manner described above in Test Method A and was allowed to dry as described Test Method A. An 8"×10" piece of Grade 80 bleached cotton cheesecloth of a 40 x 32 construction (commercially available from Twin City Janitor Supply Co., St. Paul, Minn.) was saturated with tap water of a temperature of between about 65° and 70° F., and was folded into 2"×2" pad. The pad was scrubbed across each coating using moderate pressure, a freshly-prepared pad being used for each coating. Scrubbing rate was approximately 100 single passes over the coating during a 30 second interval. The number of passes (over the surface of each coating) required to scrub through the coating was recorded. A film which is suitably water-insoluble will withstand at least about 100 single passes without being scrubbed through.

EXAMPLE 1

Preparation of a Film-Forming Composition

Step A. Prepolymer Preparation

Five hundred g of Niax ® PPG-1025 (a polypropylene glycol of molecular weight of about 1000, available from Union Carbide), 270.6 g of dicyclohexylmethane-4,4'-diisocyanate and 0.239 g of dibutyl tin dilaurate were combined in a resin flask and the resulting mixture heated at 100° C. for 4 hours under a dry inert atmosphere of nitrogen to provide the prepolymer.

Step B. Polyvinylpyrrolidone Polymer Preparation

To 200 g of anhydrous acetone was added 194 g n-vinylpyrrolidone, 6 g isocyanatoethylmethacrylate, 0.4 g azobisisobutyronitrile and 0.4 g of t-dodecylmecaptan. The mixture was heated to 55° C. and maintained at that temperature for 16 hours under a nitrogen atmosphere to provide the polyvinylpyrrolidone polymer.

Step C. Chain Extension to a Film-Forming Polymer

One hundred g of the above prepolymer and 27.2 g of the above polyvinylpyrrolidone polymer in acetone were mixed with a solution of 11.2 g of isophorone diamine in 350 g of isopropanol. The mixture was mixed for 15 minutes at 23° C. and the solvent was then removed under vacuum using a water bath maintained at 70° C. The resulting solid film-forming polymer was redissolved in isopropanol to give a solution containing 25% solids by weight.

Step D. Incorporation of Iodine

Twenty g of iodine crystals and 24 g of sodium iodide were dissolved in 56 g of ethanol. To 100 g of the 25% solids solution of the film-forming polymer was added 2.5 g of the iodine-iodide solution. The mixture was mixed until dissolution was achieved and the resulting solution was used in the following studies.

When the above composition was applied to skin, a 4-minute tack-free time was observed and the resulting film adhered suitably to skin.

A 5"×8" patch of a film about 1-mil in thickness is removable from skin intact.

A film which was solvent-cast onto release paper and had a thickness of about 1-mil (0.0025 centimeter) when dry exhibited a tensile strength of 3500 psi and an elongation of 300%.

A film which was solvent-cast onto release paper and had a thickness of 1.2-mil (0.003-centimeter) when dry exhibited a moisture vapor transmission rate of 1500 grams/meter$^2$/24 hours when measured at 40° C. using a 80% relative humidity differential across the film.

Both the liquid composition of this Example and a cured film obtained therefrom suitably retained iodine.

The film retained iodine (as determined visually) after 2 days at 60° C. under a reduced pressure provided by a water aspirator.

A 1-mil thick (0.0025-centimeter-thick) antimicrobial film obtained using the composition of this Example and a control film of equal thickness and comprising the above film-forming polymer and no iodine were cut into one inch squares. The squares of film were placed in the bottom of a moist chamber and coated with 0.05 ml of a saline suspension of S. Faecalis. At intervals of 30, 45 and 90 minutes, the films were removed, placed in blenders containing 0.1% sodium thiosulfate to neutralize residual iodine, and macerated for 5 minutes. An aliquot of each homogenate was serially diluted and the dilutions were plated in nutrient agar comprising 10 cc of the M-enterococcus media "Difco Media 6785" (commercially available from Difco Laboratory). Plate colony counts were made after incubation at 37° C. for 48 hours. The log 10 reduction in organism colony numbers was determined by calculating the numerical difference between colony counts from the antimicrobial film test plates and colony counts from the control film test plates. When tested in the above manner the antimicrobial film exhibited a 5 log reduction in colony numbers of S. Faecalis at 30, 45 and 90 minutes.

An antimicrobial film obtained using the composition of this Example also exhibited excellent antimicrobial activity against both *Staphylococcus aureus* and *Escherichia coli* organisms which had been seeded on human skin.

EXAMPLE 2

Preparation of an Alternative Iodine-Containing Liquid Composition

A polymer was prepared by free-radical-polymerizing n-vinylpyrrolidone and 2-vinyl-4,4-dimethyl-2-oxazolin-5-one in accordance with the procedure of Step B of Example 1. Amounts of n-vinylpyrrolidone, azobisisobutyronitrile, and t-dodecylmercaptan were as indicated in Example 1 and 2-vinyl-4,4-dimethyl-2-oxazolin-5-one was employed in the amount of 6 g.

One hundred g of the prepolymer prepared in Step A of Example 1 and 24.6 g of the above polyvinylpyrrolidone polymer-containing solution were mixed together with 270 g of isopropanol. A solution of 11 g of 3-aminomethyl-3,5,5-trimethylcyclohexylamine in 50 g of isopropanol was added to the resulting solution within about two minutes.

Iodine was incorporated into the composition following the procedures of Step D of Example 1 except that here 2.7 g of the iodine-iodide solution was employed instead of the 2.5 g which was employed in Example 1. The resulting composition was used in the following study.

A film which was solvent-cast onto release paper and had a thickness of about 1-mil (0.0025 centimeter) exhibited a tensile strength of 2500 psi and an elongation of 330%.

EXAMPLES 3-4

Film-forming polymers were prepared in accordance with the procedures of Example 1 using the following ingredients in the indicated amounts (Table I below) to provide a 25% solids solution of the respective film-forming polymer:

TABLE I

| | Parts by weight (grams) | | |
|---|---|---|---|
| | Prepolymer of Example 1 | Polyvinylpyrrolidone Polymer of Example 1 | Isophorone diamine |
| Example 3 | 100 | 5.5 | 10.8 |
| Example 4 | 100 | 21.3 | 10.8 |

To 100 g of each of the 25% solids solutions of Examples 4 and 5 was added 5.3 and 5.8, respectively, of the iodine-iodide solution of Example 1 (Step D).

Films which were solvent-cast onto paper from the above compositions and had a thickness of about 1-mil (0.0025-centimeter) when dry exhibited the following tensile strengths and elongation values (Table II below):

TABLE II

| | Tensile Strength (pounds per square inch) | Elongation |
|---|---|---|
| Composition of Example 3 | 3700 | 350% |
| Composition of Example 4 | 3100 | 320% |

EXAMPLE 5

Preparation of yet another Alternative Film-Forming Composition

One hundred and fifty g of the prepolymer of Example 1 (Step A) and 41.70 g of the solution of the polyvinylpyrrolidine polymer in acetone prepared in Example 1 (Step B) were mixed with a solution of 17.07 g of isophorone diamine in 660 g of isopropanol. The mixture was mixed for 15 minutes at 23° C.

To 868.77 g of the above 21% solids solution of the film-forming polymer was added slowly a mixture of 54.63 g of the iodine-iodide solution of Example 1 (Step D) and 1009.50 g of ethanol. The resulting mixture was mixed until dissolution was achieved and the resulting 11% solids solution was used in the following studies.

A film which was solvent-cast onto release paper and had a tackiness of about 1-mil (0.0025 centimeter) when dry exhibited a tensile strength of 3900 psi and an elongation of 220% when tested in accordance with ASTM-D-638-80 using a 20 inch per minute jaw separation rate.

The antimicrobial activity exhibited by the film-forming composition of this Example was determined as follows. An overnight culture of S. faecalis on tryptone soy agar was suspended in sterile saline (0.85%) to a density of 40% T @ 660 nanometers. Two ml of this suspension was evenly dispersed over the filter of a Nalge analytical filter unit type A (0.2 micron), which was then evacuated for 2 minutes. With the vacuum on, 0.4 ml of the film-forming composition was applied to the filter surface and evenly dispersed with an artists brush of natural bristle (Grumbacher eterna #10) which has been precleansed in isopropanol. The distribution of the sample over the filter surface required approximately 10 seconds. Each treated filter was held for an exposure interval of 1 or 2 or 30 or 90 minutes. The disposable filter units were then unlocked, and each filter was aseptically removed, placed in blenders containing 100 ml of sterile 0.1% sodium thiosulfate solution, and macerated for 5 minutes. An inoculated filtration unit evacuated for approximately 2 minutes was employed as an index of microbial load; this represents zero-time exposure to specific antimicrobial treatment. Prepared plates were incubated at 37° C. for 48 hours to ensure colony development. The following Table II lists the log reduction in colony numbers of S. Faecalis at 1, 2, 30 and 90 minutes for the film-forming composition of this invention both before and after gamma irradiation at about 2.64–2.83 mrad. Table II also lists the log reduction in colony numbers for Betadine ® (a 10% aqueous solution of polyvinylpyrrolidone-iodine complex, available from Purdue-Frederick).

TABLE II

| Time (minutes) | Unirradiated Film-forming Composition of this Example | Irradiated Film-forming Composition of this Example | Betadine ® |
|---|---|---|---|
| 1 | 7.3 | 8 | 0.9 |
| 2 | 5.8 | 8 | 2.7 |
| 30 | not determined | 8 | 8 |
| 90 | 8 | 8 | 8 |

The log reduction in colony numbers observed with the film-forming composition of this Example at 1 and 2 minutes is believed to be attributable to both the alcohol contained in that composition as well as the iodine itself.

EXAMPLES 6-11 AND COMPARATIVE EXAMPLES A-C

Compositions comprising various film-forming polymers and iodine were prepared in accordance with the procedures of Example 5 using the following ingredients in the indicated amounts (Table III below):

TABLE III

| | Parts by weight (grams) | | | |
|---|---|---|---|---|
| Example | Prepolymer of Example 1 | Solution of Polyvinylpyrrolidone Polymer of Example 1 | Isophorone Diamine (in indicated amount of isopropanol) | Iodine solution of Example 1 (in indicated amount of ethanol) |
| 6 | 30 | 8.34 | 3.37 (78.0) | 10.91 (78.0) |
| 7 | 30 | 8.34 | 2.50 (78.0) | 10.91 (78.0) |
| 8 | 30 | 8.34 | 1.66 (78.0) | 10.91 (78.0) |
| 9 | 30 | 2.09 | 3.37 (78.0) | 10.91 (201.62) |
| 10 | 15 | 10.46 | 1.69 (77.6) | 5.46 (100.8) |
| 11 | 15 | 7.44 | 1.69 (74.7) | 5.46 (100.8) |
| Comparative Example A | 30 | 8.34 | 0.88 (78.0) | 10.91 (78.0) |
| Comparative Example B | 30 | 83.34 | 3.37 (198.28) | 10.91 (201.62) |
| Comparative Example C | 30 | 41.67 | 3.37 (161.37) | 10.91 (201.62) |

One hundred g of each of the compositions of Examples 6-8 and Comparative Example A were further diluted with a mixture of 25.8 g of isopropanol and 54.3 g of ethanol to provide solutions containing 10.9% by weight solids. Compositions of Example 9-11 and Comparative Examples B and C already contained 10.9% by weight solids as prepared above and therefore were not diluted further.

When tested in accordance with Test Method A above, the compositions of Examples 6-11 formed coatings which dried suitably to a tack-free state as determined by the absence of any cotton fibers adhered to each coating. The films all would exhibit an elongation of at least about 150%

When tested in accordance with Test Method B, the compositions of Examples 6-11 provide coatings exhibiting suitable water-insolubility since each withstood 100 passes without exhibiting any visual change in integrity.

While the composition of Comparative Example A provided a coating which withstood greater than 100 passes without any visual change in its integrity (as determined by Test Method B), the coating did not suitably dry to a tack-free state as determined by the adherence thereto of cotton fibers when tested in accordance with Test Method B. The compositions of Comparative Examples B and C, on the other hand, provided coatings which dried suitably to a tack-free state (as determined by Test Method A), but which were not suitably water-insoluble as determined by Test Method B. Specifically, the compositions of Comparative Examples B and C were scrubbed through after about 1 and 60 passes respectively.

Betadine ®, when tested in accordance with Test Methods A and B, provided a film which was suitably tack-free but dissolved after a single pass.

COMPARATIVE EXAMPLES D-F

Compositions comprising various film-forming polymers (prepared from the above prepolymer) and iodine were prepared in accordance with the procedures of Example 5 using the following ingredients in the indicated amounts (Table IV below):

TABLE IV

| | | Parts by weight (grams) | | |
|---|---|---|---|---|
| Example | Prepolymer | Solution of Polyvinylpyrrolidone Polymer of Example 1 | Isophorone Diamine (in indicate amount of isopropanol) | Iodine solution of Example 1 (in indicated amount of ethanol) |
| Comparative Example D | 30 | 8.34 | 1.10 (78.0) | 10.91 (78.0) |
| Comparative Example E | 30 | 8.34 | 0.83 (78.0) | 10.91 (78.0) |
| Comparative Example F | 30 | 8.34 | 0.55 (78.0) | 10.91 (78.0) |

One hundred g of each of the compositions of Comparative Examples D-F were further diluted with a mixture of 25.8 g of isopropanol and 54.3 g of ethanol to provide solutions containing 10.9% by weight solids.

When tested in accordance with Test Method B, the compositions of Comparative Examples D and E resulted in coatings which were suitably water-insoluble as evidenced by the fact that the coating withstod 100 passes without being scrubbed through. The composition of Comparative Example F, on the other hand, provided a coating which was scrubbed through after only about 40 passes. Also, when tested in accordance with above Test Method A, the compositions of Comparative Examples D-F all failed to dry suitably to a tack-free state as evidenced by the adherence of cotton fibers thereto.

COMPARATIVE EXAMPLES G-I

A prepolymer was prepared by combining 500 g of Niax ® PPG-3025 (a polypropylene glycol of molecular weight of about 3000, available from Union Carbide), 88.3 g of dicyclohexylmethane-4,4'-diisocyanate and 0.24 g of dibutyl tin dilaurate in a resin flask, and heating the resulting mixture at 100° C. for 4 hours under a dry inert atmosphere of nitrogen.

Compositions comprising various film-forming polymers (prepared from the above prepolymer) and iodine were prepared in accordance with the procedures of Example 5 using the following ingredients in the indicated amounts (Table V below):

TABLE V

| | | Parts by weight (grams) | | |
|---|---|---|---|---|
| Example | Prepolymer | Solution of Polyvinylpyrrolidone Polymer of Example 1 | Isophorone Diamine (in indicated amount of Isopropanol) | Iodine solution of Example 1 (in indicated amount of ethanol) |
| Comparative Example G | 30 | 8.34 | 1.13 (78.0) | 10.91 (78.0) |
| Comparative Example H | 30 | 8.34 | 0.85 (78.0) | 10.91 (78.0) |
| Comparative Example I | 30 | 8.34 | 0.56 (78.0) | 10.91 (78.0) |

A prepolymer was prepared by combining 500 g of Niax ® PPG-4025 (a polypropylene glycol of molecular weight of about 4000, available from Union Carbide), 67.3 g of dicyclohexylmethane-4,4'-diisocyanate and 0.23 g of dibutyl tin dilaurate in a resin flask, and heating the resulting mixture at 100° C. for 4 hours under a dry inert atmosphere of nitrogen.

One hundred g of each of the compositions of Comparative Examples G-I were further diluted with a mixture of 25.8 g of isopropanol and 54.3 g of ethanol to provide solutions containing 10.9% by weight solids.

When tested in accordance with Test Method B, the compositions of Comparative Example G-I resulted in films which were suitably water-insoluble as evidenced by the fact that each film withstood 100 passes without being scrubbed through. However, when tested in accordance with Test Method A, the compositions of Comparative Examples G–I all failed to dry suitably to a tack-free state as evidenced by the adherence of cotton fibers thereto.

What is claimed is:

1. A dermatologically acceptable, film-forming composition, comprising:

(a) a film-forming polymer which is the reaction product of (i) a prepolymer having a plurality of isocyanate functionalities, said prepolymer being the reaction product of a polyisocyanate, a major amount of which by weight is diisocyanate, and an isocyanate-reactive compound having a plurality of functionalities selected from the group consisting of a hydroxy group, a primary amine group, a secondary amine group, a thiol group, and a combination of at least two of the foregoing, a major amount of said isocyanate-reactive compound being difunctional with respect to said functionalities contained therein; (ii) a polyvinylpyrrolidone polymer which is the free-radical polymerization reaction product of at least n-vinylpyrrolidone and a vinyl-functional compound; and (iii) a chain-extender for said prepolymer and said polyvinylpyrrolidone polymer, said chain-extender having a plurality of functionalities selected from the group consisting of a hydroxy group, a primary amine group, a secondary amine group, a thiol group, and a combination of at least two of the foregoing, a major amount of said chain-extender being difunctional with respect to said functionalities contained therein; said vinyl-functional compound being further characterized in that it contains a functionality having reactivity with said chain-extender which is substantially equivalent to reactivity of the isocyanate functionalities of said prepolymer with said chain-extender; and (b) as an antimicrobial agent, iodine which forms a complex with said film-forming polymer;

said composition when applied to skin from a fugitive solvent being capable of forming a substantially water-insoluble, substantially tack-free, flexible film which adheres to skin, releases iodine, when said film is in contact with the skin, and exhibits an elongation of between about 150% and 1000%.

2. A composition in accordance with claim 1, wherein said prepolymer is the reaction product of a diisocyanate with an isocyanate-reactive compound selected from the group consisting of a diol having a molecular weight of between about 750 and 2500 and a diamine having two primary amine groups and having a molecular weight of between about 750 and 2500.

3. A composition in accordance with claim 2, wherein said isocyanate-reactive compound is a diol which is selected from the group consisting of a polyether diol and a polyester diol and wherein said diisocyanate is an aliphatic diisocyanate.

4. A composition in accordance with claim 1, wherein said polyvinylpyrrolidone polymer is the free-radical-polymerization reaction product of n-vinylpyrrolidone and an isocyanate-functional acrylate or methacrylate.

5. A composition in accordance with claim 4, wherein said polyvinylpyrrolidone polymer is prepared from said n-vinylpyrrolidone and said isocyanate-functional acrylate or methacrylate in a weight ratio of from about 99:1 to 90:10.

6. A composition in accordance with claim 1, wherein said polyvinylpyrrolidone polymer is the free-radical-polymerization reaction product of n-vinylpyrrolidone and a vinyl-functional azlactone.

7. A composition in accordance with claim 6, wherein said polyvinylpyrrolidone polymer is prepared from said n-vinylpyrrolidone and said vinyl-functional azlactone in a weight ratio of from about 99:1 to 90:10.

8. A composition in accordance with claim 1, wherein said chain-extender is selected from the group consisting of a diamine having two primary amine groups and a diol.

9. A composition in accordance with claim 8, wherein said chain-extender is selected from the group consisting of an aliphatic diamine having two primary amine groups and a diol.

10. A composition in accordance with claim 1, wherein the weight ratio of the amount of the polyvinylpyrrolidone polymer employed to the amount of the prepolymer employed in preparing said film-forming polymer is from about 2:98 to 20:80 and said chain-extender is employed in the amount of about 0.4 to 1 equivalents per equivalent of the sum total of reactive functionality of said prepolymer and said polyvinylpyrrolidone polymer.

11. A composition in accordance with claim 10, wherein the weight ratio of the amount of the polyvinylpyrrolidone polymer employed to the amount of the prepolymer employed in preparing said film-forming polymer is from about 5:95 to 15:85.

12. A composition in accordance with claim 11, wherein the weight ratio of the amount of the polyvinylpyrrolidone polymer employed to the amount of the prepolymer employed in preparing said film-forming polymer is from about 7:93 to 12:88.

13. A composition in accordance with claim 1, further comprising an alcohol selected from the group consisting of ethanol and isopropanol, said film-forming polymer being dissolved in said alcohol.

14. A composition in accordance with claim 1, wherein said composition when applied to skin from a fugitive solvent is capable of forming a film which exhibits a tensile strength of at least about 1500 psi and an elongation of between about 150% and 1000%.

15. A composition in accordance with claim 1, wherein said composition when applied to skin from a fugitive solvent is capable of forming a film which exhibits a tensile strength of at least about 2000 psi and an elongation of between about 200% and 1000%.

16. A composition in accordance with claim 1, wherein said composition when applied to skin from a fugitive solvent is capable of forming a film which exhibits a tensile strength of at least about 2500 psi and an elongation of between about 250% and 1000%.

17. A method of promoting asepsis on mammalian skin, comprising the steps of:

(a) applying to said skin said composition of claim 1; and (b) allowing said composition to dry to form said film.

18. The method in accordance with claim 17, wherein said film is peeled substantially intact from said skin once the need for asepsis has discontinued.

19. The method in accordance with claim 17, wherein said film is removed from said skin using a remover solution once the need for asepsis has discontinued.

20. The method in accordance with claim 17, wherein said film is allowed to wear off once the need for asepsis has discontinued.

* * * * *